United States Patent [19]

Biscoping et al.

[11] Patent Number: 4,994,036

[45] Date of Patent: Feb. 19, 1991

[54] CATHETER SET FOR SPINAL ANAESTHESIA

[75] Inventors: Juergen Biscoping, Giessen; Marie-Louise Summerer, Koerle; Heinz Wiegel, Alheim; Hans-Hinrich Witt, Koerle, all of Fed. Rep. of Germany

[73] Assignee: B. Braun Melsungen AG, Melsungen, Fed. Rep. of Germany

[21] Appl. No.: 390,608

[22] Filed: Aug. 7, 1989

[30] Foreign Application Priority Data

Sep. 9, 1988 [DE] Fed. Rep. of Germany ... 8811408[U]

[51] Int. Cl.$^5$ ............................................. A61M 5/178
[52] U.S. Cl. ..................................... 604/158; 604/164; 604/272; 604/51
[58] Field of Search ............... 604/280, 281, 164, 158, 604/159, 165, 166, 170, 171, 272, 264, 51

[56] References Cited

U.S. PATENT DOCUMENTS

| | | | |
|---|---|---|---|
| 2,922,420 | 11/1957 | Chery | 604/158 |
| 4,230,123 | 10/1980 | Hawkins, Jr. | 128/658 |
| 4,518,383 | 5/1985 | Evans | 604/164 |
| 4,573,448 | 3/1986 | Kambin | 604/51 |
| 4,650,472 | 3/1987 | Bates | 604/158 |
| 4,721,506 | 1/1988 | Teves | 604/158 |
| 4,737,146 | 4/1988 | Amaki et al. | 604/158 |
| 4,808,157 | 2/1989 | Coombs | 604/156 |

*Primary Examiner*—C. Fred Rosenbaum
*Assistant Examiner*—Kathleen A. Daley

[57] ABSTRACT

A spinal cannula adapted for insertion into an epidural cannula that may be advanced up to the dura. In placing the end of the spinal cannula intrathecally, the dura is pierced by the spinal cannula. Then, a guide wire is advanced to that intrathecal position through the spinal cannula. After removal of the spinal cannula, a spinal catheter is advanced over the guide wire and within the epidural cannula. The epidural cannula imparts the necessary directional stability to the catheter upon its advancement and facilitates the passage through the dura already perforated by the spinal cannula.

11 Claims, 3 Drawing Sheets

CATHETER SET FOR SPINAL ANAESTHESIA

BACKGROUND OF THE INVENTION:

1. Field of the Invention:

The invention relates to a catheter set for spinal anaesthesia.

2. Description of Related Art

Spinal catheters are commonly placed intrathecally via a cannula. The dura is first punctured with a spinal or an epidural cannula. Subsequently, a spinal catheter is inserted through the epidural cannula.

A difficulty arising in this procedure is that the spinal or the epidural cannula must have a small diameter in order to minimize the damage done to the dura and the resulting postspinal headache. On the other hand, the spinal or the epidural cannula must have a diameter large enough to allow the passage of the spinal catheter. However, there are no connectors for very thin spinal catheters, which would allow a tight catheter-connector connection. Due to these difficulties, use is presently made of spinal or epidural cannulas with a diameter larger than 0.65 mm (23 G).

It is an object of the present invention to provide a catheter set that, upon puncturing the dura, causes a minimum opening therein, but which allows for the use of a comparatively thick spinal catheter.

SUMMARY OF THE INVENTION

In accordance with the present invention, this and other objectives are achieved by providing a catheter set including a spinal cannula insertable into the epidural cannula and a guide wire advanceable through the spinal cannula. The front end of the spinal cannula projects out of the epidural cannula in its inserted state. The diameter of the guide wire is smaller than the inner diameter of the spinal catheter.

With the catheter set according to the present invention, the epidural cannula is first advanced up to the outer wall of the dura. Subsequently, the thinner spinal catheter is inserted into the epidural cannula in order to perforate the dura therewith. Upon reaching the spinal space with the spinal cannula, the mandrin of the spinal cannula is pulled out, the guide wire is inserted into the spinal cannula, the spinal cannula is pulled out over the guide wire and the spinal catheter is pushed over the guide wire. The insertion of the catheter over the guide wire is performed in a manner similar to the insertion of a catheter into a blood vessel, following the known Seldinger method. After the catheter tip has reached the spinal space, the guide wire and the epidural cannula are withdrawn.

One purpose of the comparatively thick epidural cannula is to keep the perforation channel through the muscle tissue open and to impart the necessary directional stability to the catheter during the advancement thereof. Further, the epidural cannula encloses the spinal catheter while it is inserted. Thus, the advancement of the spinal cannula is not hindered by the surrounding tissue. Only when the tip of the spinal cannula meets the dura does a clearly tangible resistance occur. Perforating the dura may be performed subsequently by a careful advancement of the spinal cannula.

It is a significant advantage of the present invention that the point of perforation of the dura is of a minimum diameter, the catheter being advanced into the point of perforation only after the spinal cannula with which the perforation has been performed is withdrawn. Thus, it is possible to insert a catheter into a perforation opening that fills this opening entirely, the injury of the dura being kept at a minimum.

Preferably, the spinal cannula contains an extractable mandrin. Upon perforating the spinal space, the mandrin is located in the spinal cannula. After the perforation, the mandrin is pulled out. The spinal space may be identified by the liquid flowing back.

The guide wire used is preferably very thin (approximately 0.25mm) and preferably has a flexible tip. It may also be coated with plastic. The guide wire is advanced through the spinal cannula and serves as a guide element for the spinal catheter advanced through the epidural cannula, after the spinal cannula has been pulled out.

In one embodiment of the invention the epidural cannula is provided with a handle portion and the cannula tube protrudes from the handle portion at the rear end and is provided there with an enlargement. This facilitates the insertion of the spinal catheter into the cannula tube of the epidural cannula. Although the cannula tube is slightly funnelled at its rear end, it will fit into the hub of a syringe that may be connected to the epidural cannula.

BRIEF DESCRIPTION OF THE DRAWINGS

A detailed description of a preferred embodiment of the invention will be made with reference to the accompanying drawings.

DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

Figure 1:
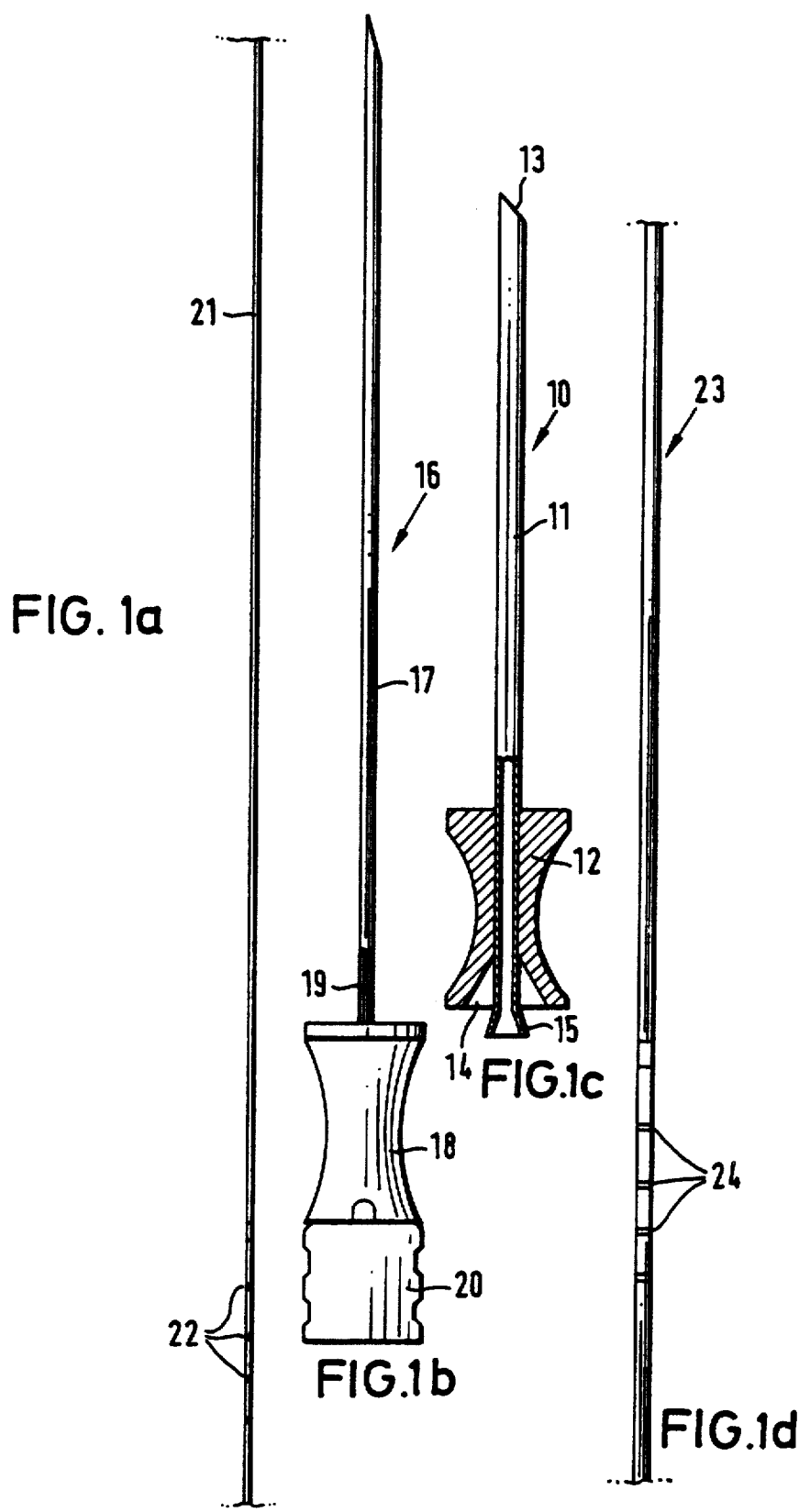
FIG. 1 shows the components of a catheter set in accordance with a preferred embodiment of the present invention.
Figure 2:
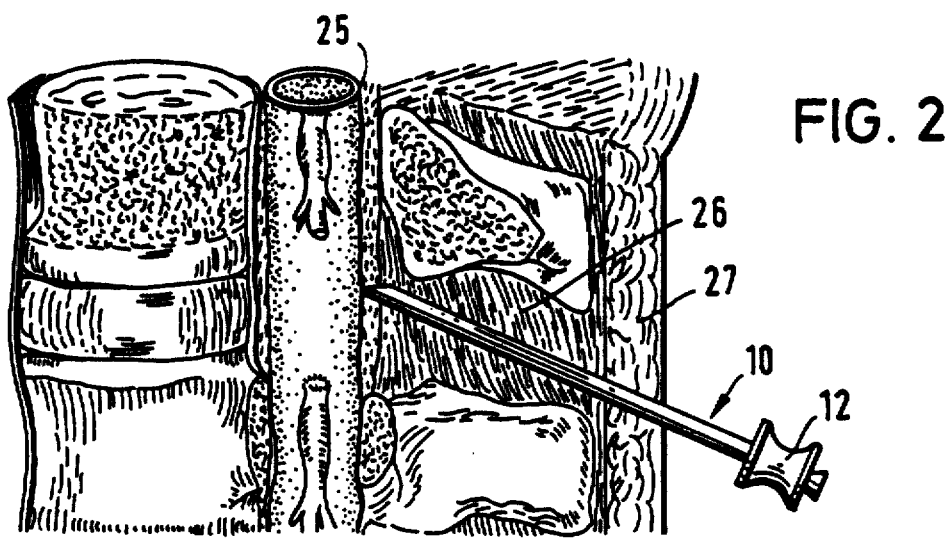
FIGS. 2 to 7 show different phases in the use of the catheter set.

As illustrated in FIG. 1, an epidural cannula 10 is provided consisting of a cannula tube 11 and a handle portion 12 (or a cannula hub). The epidural cannula is also referred to as Crawford-cannula. The front tip of the cannula hub is provided with a ground portion 13 suited for the puncturing of tissue. The epidural cannula 10 may have the dimensions 0.7×0.9×80mm, the first number representing the inner diameter, the second number representing the outer diameter and the third number representing the free length of the cannula hub.

A funnel-shaped trough 14 is formed at the rear end of the handle portion 12. The rear end of the cannula tube 11 extends through the trough 14 and even beyond it. A funnel-shaped enlargement 15 is provided at the rear end of the cannula tube 11 for facilitating the insertion of the spinal catheter. The handle portion 12 is formed as a connecting element with the trough 14 for connecting a syringe (not shown).

The spinal cannula 16 preferably has the following dimensions: 0.35×0.55×120mm, the numbers representing the same dimensions as previously explained for the epidural cannula. At the rear end of the cannula tube 17, a handle portion 18 is provided. A mandrin 19 is located in the spinal cannula 16 that extends throughout the handle portion 18 and is provided with a handle 20 at its rear end.

The catheter set further comprises a guide wire 21 having a flexible tip. This guide wire may have the dimensions of, e.g., 0.25×900mm, the first number representing the diameter and the second number representing the length. The guide wire 21 is provided with markers 22 for determining the path of advancement.

The spinal catheter 23 consists of an elongate flexible catheter hose with the following dimensions: 0.30×0.60×600mm. The outer diameter of the spinal catheter 23 is substantially equal to that of the spinal cannula 16. In the vicinity of the rear of the spinal catheter 23, end markers 24 are provided for controlling the path of insertion.

The handling of the catheter set described above is illustrated in FIGS. 2 to 7.

First, the skin 27 and the muscle tissue 26 are perforated with the epidural cannula 10, until the ground portion of the epidural cannula 10 abuts the outer side of the dura 25.

Figure 3:
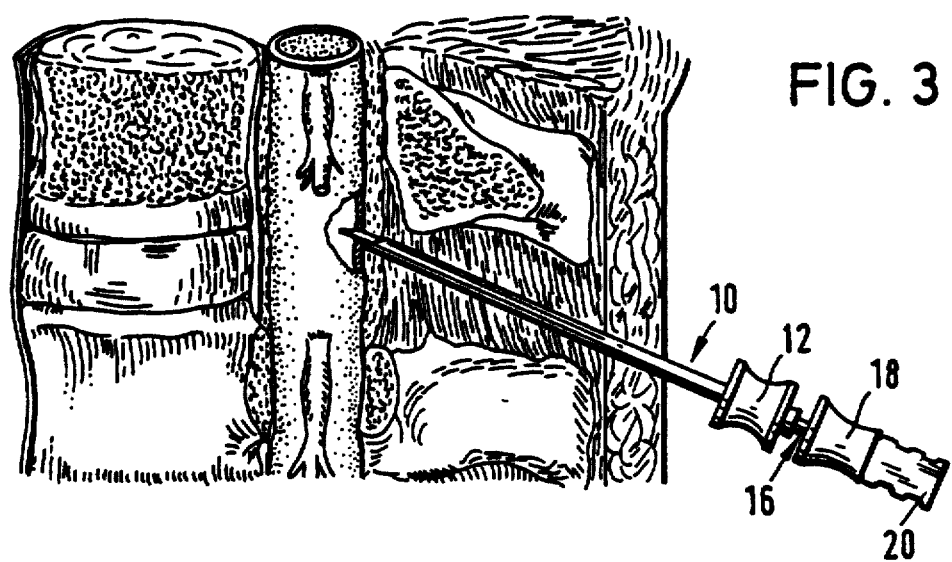

As shown in FIG. 3, the spinal cannula 16 with the mandrin 19 situated therein is inserted into the epidural cannula until it reaches an intrathecal position. In doing so, the front end of the spinal cannula pierces the dura 25.

Figure 4:
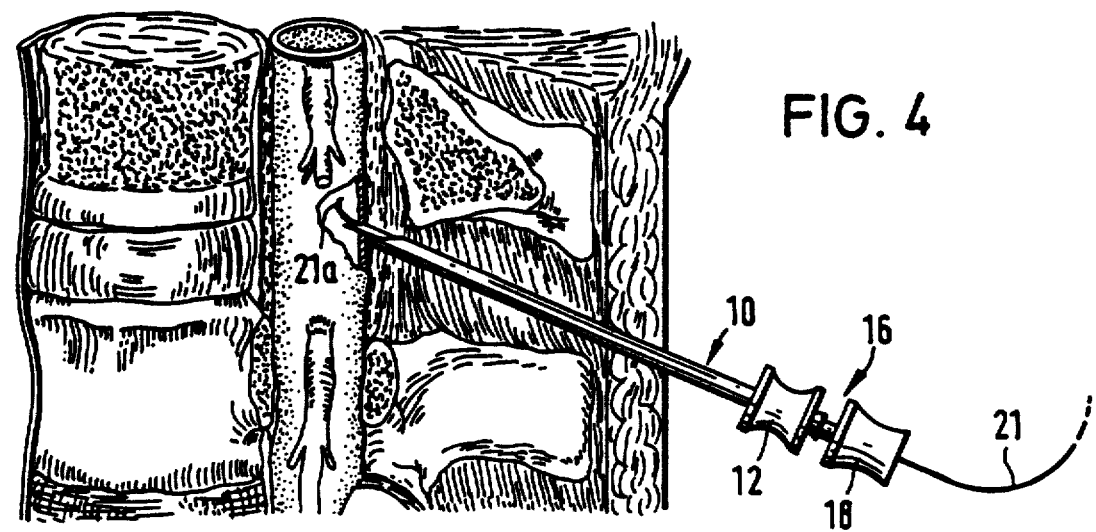

FIG. 4 illustrates the way in which the guide wire 21 is advanced through the spinal cannula 16 lying in the epidural cannula 10, after the mandrin 19 has been pulled out. The soft end 21a of the guide wire 21 projects from the front end of the spinal cannula 16 piercing the dura 25.

Figure 5:
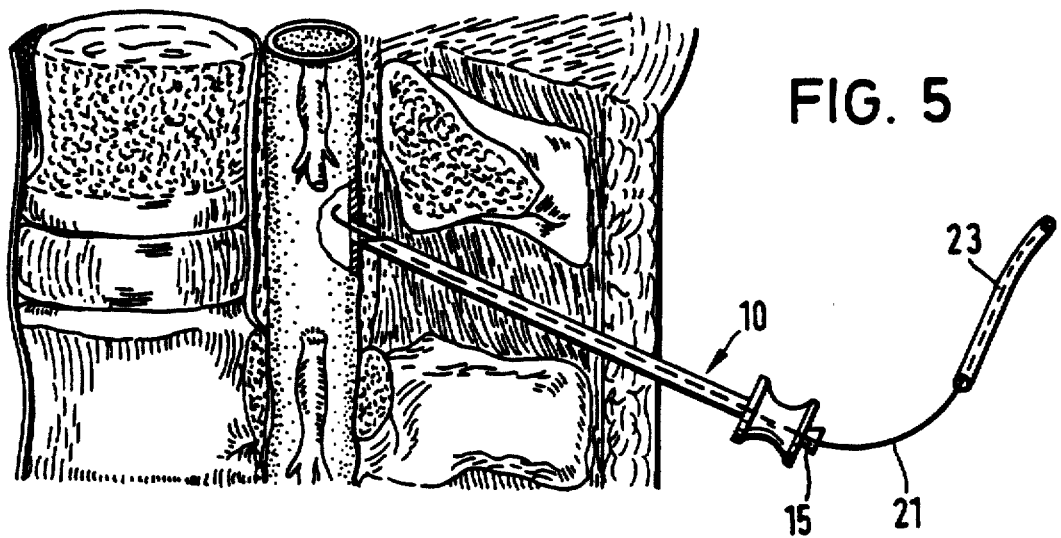

After the spinal cannula 16 has been withdrawn over the rear end of the guide wire 21 and after its removal from the epidural cannula 10, the catheter 23 is set on the guide wire 21, as shown in FIG. 5, and inserted into the epidural cannula 10 over the guide wire 21. The funnel-shaped enlargement 15 facilitates the insertion of the catheter into the rear end of the cannula tube 11.

Figure 6:
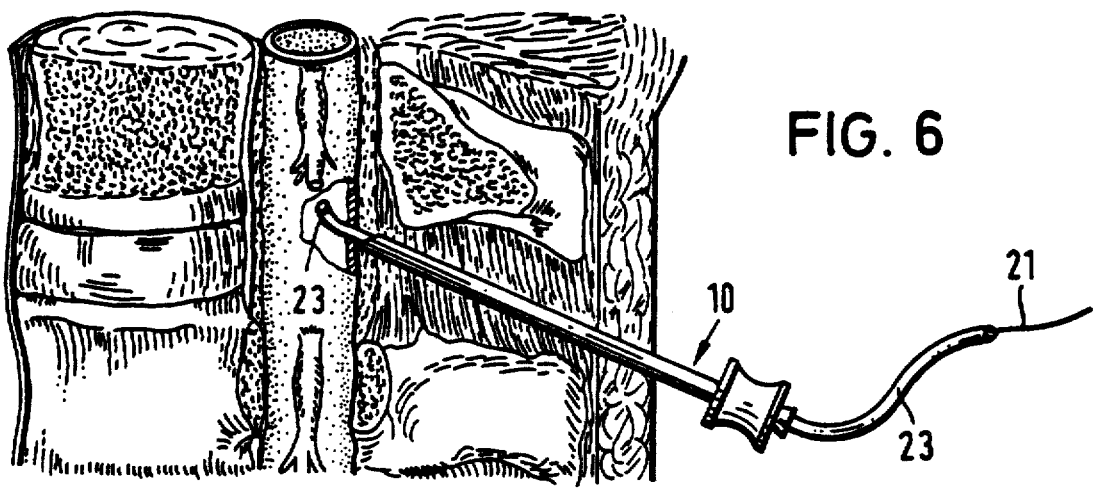
Figure 7:
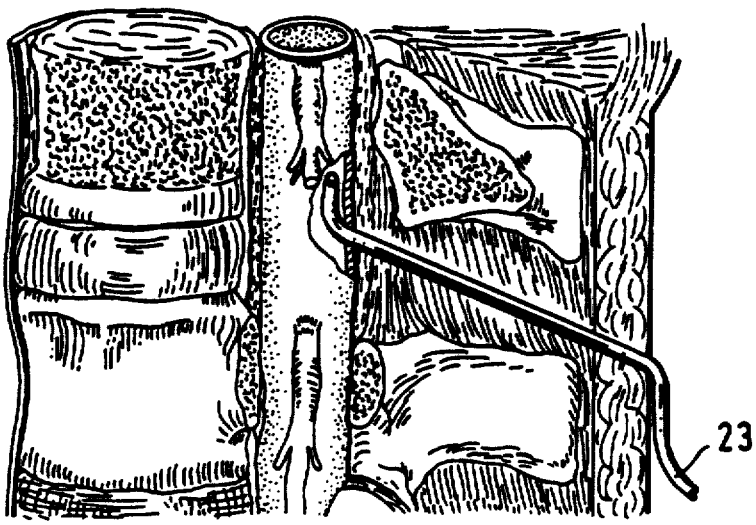

After the catheter 23 is in an intrathecal position, the guide wire 21 is withdrawn from the catheter, as illustrated in FIG. 6. Subsequently, the epidural cannula 10 is removed over the spinal catheter 23. If necessary, the catheter may be tunneled. Finally, a connector (not shown) is connected to the rear end of the catheter in order to allow an intrathecal injection.

The presently disclosed embodiment is therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A catheter set for spinal anaesthesia, comprising:
   an epidural cannula having a lumen having an inner diameter smaller than approximately 1.0 mm,
   a spinal catheter having an inner diameter and being adapted for insertion into the lumen of the epidural cannula,
   a spinal cannula adapted for insertion into the lumen of the epidural cannula, the spinal cannula having a front end adapted to project out of the epidural cannula when the spinal cannula is inserted into the lumen of the epidural cannula, and
   a guide wire adapted for insertion into the spinal cannula, the guide wire having a diameter which is smaller than the inner diameter of the spinal catheter,
   whereby the spinal cannula is removable from the lumen of the epidural cannula over the guide wire, and
   whereby the spinal catheter is insertable into the lumen of the epidural cannula over the guide wire.

2. The catheter set according to claim 1, further comprising a withdrawable mandrin adapted to be contained in the spinal cannula.

3. The catheter set according to claim 1, wherein the epidural cannula includes an enlarged portion at one end thereof, and further comprising:
   a handle provided on the epidural cannula, the handle having a rear end through which the enlarged portion of the epidural cannula protrudes.

4. The catheter set according to claim 3, wherein the rear end of the handle defines a trough from which the epidural cannula projects.

5. The catheter set according to claim 1, wherein the spinal cannula has an outer diameter which is less than approximately 0.6 mm.

6. The catheter set according to claim 1, wherein the epidural cannula has an inner diameter which is equal to approximately 0.7 mm.

7. The catheter set according to claim 1, wherein the epidural cannula 10 has a cannula tube 11 having a length approximately equal to 80 mm.

8. The catheter set according to claim 1, wherein a portion of the spinal cannula protrudes from the epidural cannula by approximately 10 mm to 20 mm when the spinal cannula is inserted into the epidural cannula.

9. The catheter set according to claim 1, wherein the epidural cannula comprises a handle adapted for connection to a syringe.

10. A method of spinal anaesthesia comprising the steps of:
    advancing an epidural cannula to the dura,
    inserting a spinal cannula into the epidural cannula,
    penetrating the dura with the spinal cannula,
    inserting a guide wire into the spinal cannula,
    removing the spinal cannula from the epidural cannula over the guide wire,
    inserting a spinal catheter into the epidural cannula over the guide wire to an intrathecal position,
    removing the guide wire from the spinal catheter,
    removing the epidural cannula over the spinal catheter.

11. A method of spinal anaesthesia comprising the steps of:
    advancing an epidural cannula to the dura,
    inserting a spinal cannula having a mandrin therein into the epidural cannula,
    penetrating the dura with the spinal cannula,
    removing the mandrin from the spinal cannula,
    inserting a guide wire into the spinal cannula,
    removing the spinal cannula from the epidural cannula over the guide wire,
    inserting a spinal catheter into the epidural cannula over the guide wire to an intrathecal position,
    removing the guide wire from the spinal catheter,
    removing the epidural cannula over the spinal catheter.

* * * * *